United States Patent [19]

Van Wijnendaele et al.

[11] Patent Number: 4,649,192
[45] Date of Patent: Mar. 10, 1987

[54] METHOD FOR THE ISOLATION AND PURIFICATION OF HEPATITIS B SURFACE ANTIGEN USING POLYSORBATE

[75] Inventors: Frans Van Wijnendaele, Ottenburg; Guy Simonet, Perwez, both of Belgium

[73] Assignee: Smith Kline-RIT, Belgium

[21] Appl. No.: 739,415

[22] Filed: May 30, 1985

[51] Int. Cl.$^4$ .................. A61K 39/29; C07K 3/18; C07K 3/28

[52] U.S. Cl. ..................... 530/371; 424/89; 530/380; 530/415; 530/806; 530/826; 530/808

[58] Field of Search .......... 424/89; 260/112 R, 112 B; 530/380, 371, 415, 806, 826, 808

[56] References Cited

U.S. PATENT DOCUMENTS

| | | | |
|---|---|---|---|
| 4,102,996 | 7/1978 | McAleer et al. | 424/89 |
| 4,113,712 | 9/1978 | Funakoshi | 530/380 |
| 4,118,479 | 10/1978 | Prince et al. | 424/89 X |
| 4,136,094 | 1/1979 | Condie | 530/387 X |
| 4,234,564 | 11/1980 | McAleer et al. | 424/89 X |
| 4,314,997 | 2/1982 | Shanbrom | 424/101 |
| 4,315,919 | 2/1982 | Shanbrom | 424/101 X |
| 4,481,189 | 11/1984 | Prince | 424/101 |
| 4,554,157 | 11/1985 | Skelly et al. | 424/89 |
| 4,565,697 | 1/1986 | Ohmura et al. | 424/89 |

FOREIGN PATENT DOCUMENTS

| | | |
|---|---|---|
| 0072318 | 8/1982 | European Pat. Off. . |
| 0073657 | 8/1982 | European Pat. Off. . |
| 0135435 | 8/1984 | European Pat. Off. . |

OTHER PUBLICATIONS

Pillot et al., Molec. Immunol. 21(1):53 (1984).
Pillot et al., J. Clin. Microbiol. 4(3):205 (1976).
Barin et al., Ann. Microbiol. 129B:87 (1978).
Hitzeman et al., Nucl. Acids Res. 11(9):2745 (1983).

*Primary Examiner*—Howard E. Schain
*Attorney, Agent, or Firm*—Edward T. Lentz; Janice E. Williams; Alan D. Lourie

[57] ABSTRACT

The supernatant of engineered yeast cells having produced hepatitis B surface antigaen and disrupted in the presence of a polysorbate non-ionic detergent is clarified by addition of urea and adsorbed on colloidal silica from which the purified antigen is desorbed with a low ionic strength buffer supplemented with urea and a polysorbate non-ionic detergent.

9 Claims, No Drawings

METHOD FOR THE ISOLATION AND PURIFICATION OF HEPATITIS B SURFACE ANTIGEN USING POLYSORBATE

FIELD OF THE INVENTION

This invention relates to the preparation of an improved method for the isolation and purification of hepatitis B surface antigen (HBsAg) valuable for vaccinal purpose and to the preparation thereof.

The HBsAg antigen obtained by the process of the invention is in the form of 22 nm-like HBsAg particles. It is valuable for the preparation of vaccines.

BACKGROUND OF THE INVENTION

Hepatitis B is a widespread and potentially fatal viral disease. Although its etiological agent—i.e. the hepatitis B virus—has been isolated a long time ago from the blood of patients suffering of the disease, the development of a commercial hepatitis B vaccine has faced considerable drawback: hepatitis B virus is a 42 nm particle called the Dane particle consisting of (a) a core containing the viral genome bound to the core protein and containing the core antigen (HBcAg) which is not immunogenic and (b) an envelope containing the immunogenic surface antigen (HBsAg). HBsAg is a group of morphologically heterogeneous complex macromolecular structures; it contains proteins, carbohydrates, glycoproteins and lipids, the main constituents of which are phosphatidylcholine, cholesteryl ester, cholesterol and triglycerides. Infection with hepatitis B virus (HBV) leads not only to the production of Dane particles but also to overproduction of 22 nm particles and filaments containing the elements of the surface envelope. It is known that these 22 nm particles are about 1000-fold more immunogenic than the monomer HBsAg protein but the replication and expression of HBV has been hampered for a long time by the lack of an appropriate cell culture system to grow the virus in vitro. The lack of in vitro culture systems in which the virus can be efficiently propagated led to the development of searches towards either synthesis of HBsAg-like molecules or expression of HBsAg in alternative host systems by using recombinant DNA technique. For instance, expression of HBsAg has been reported from yeast cells transformed with DNA vectors bearing the gene for HBsAg and it is known that the HBsAg synthesized in yeast is assembled into particles having properties similar to the 22 nm particles secreted by human cells (P. VALENZUELA et al. Nature, 298; 347-350; 1982 and R. A. HITZEMANN et al. Nucl. Ac. Res. 11; 2745-2763; 1983). The production of HBsAg by recombinant technique is engineered cell cultures, for instance engineered yeast strains cultures is well known to the art (see for instance European Patent application publication No. 0 106 828; W. J. McALEER et al. in Nature 307; 178-180, 1984 and C. E. CARTY et al. in Abstract 030 of the annual meeting of the American Society for Microbiology 1984, 84th meeting, Mar. 4-9 1984).

Numerous articles and patents describing processes of extracting and purifying HBsAg from plasma, serum or other blood products or biological fluids or engineered cell cultures have also appeared.

The process of the invention is applicable to engineered yeast cells producing HBsAg.

The extraction and purification of HBsAg from an engineered yeast cell culture which has been grown to a satisfactory cell density generally requires 3 successive steps which are:

(1) removing HBsAg from the cell interior;
(2) enriching the medium in HBsAg;
(3) eliminating substantially all contaminants from the medium.

In most procedures, step (1) is performed by mechanical forces such as shearing forces (for example X-press or French press) or shaking the glass beads, eventually with addition of a detergent. The use of a non ionic detergent (Triton X-100) has been reported by K. MURRAY et al. in The EMBO J. 3; 645-650; 1984 and by R. A. HITZEMAN et al. loc. cit.

It has also been reported that incubation of HBsAg with detergents breaks down the particle. With that view GB Pat. No. 2 093 039 discloses treatment of HBsAg with a non ionic detergent (Triton X-100) to form a polypeptide mixture which is introduced on top of an aqueous buffer solution containing a sucrose gradient and recovering a fraction substantially free from detergent and containing micelles of the polypeptide mixture;

EP Pat. No. 0 005 864 discloses contacting antigenic mass containing hepatitis B surface antigen (HBsAg) and core antigen (HBcAg) of a particle size of at least 20 nm with a detergent (e.g. Tween 20 or 80) followed by treating the detergent containing antigenic composition with an aqueous aldehyde solution. The obtained product is a subparticulate mass having a particle size less than 20 nm especially less than 5 nm.

Japanese Patent application No. 53 104 724 (Derwent abstract 75324 A) discloses a process wherein HBsAg particles are heated in the presence of (1) a non ionic surfactant (i.e. polyoxyethylene alkylphenyl with 7-10 oxyethylene chains). (2) a protein-denaturating agent (i.e. urea or guanidine) and (3) optionally a reducing agent. The obtained product has a particle size comprised between 10 and 20 nm.

Japanese Patent application No. 50 160 420 (Derwent abstract 27420 A) discloses a process wherein HBsAg is treated with different surfactants to produce subunit products.

W. German Patent application No. 26 11 723 discloses a process wherein HBsAg spherical particles are obtained by warming the antigen in presence of a defatting surfactant.

U.S. Pat. No. 4,113,712 discloses HBsAg particles composed of single polypeptide subunits prepared by heating HBsAg in isotonic sodium chloride solution at about neutral pH containing a surfactant capable of delipidation.

U.S. Pat. No. 4,481,189 discloses a process wherein blood plasma or plasma derivative is sterilized by contact with a detergent (e.g. a non ionic detergent).

Steps (2) and (3) incorporate a variety of techniques, among which adsorption/desorption using colloidal silica, more particularly 'AEROSIL' (a product sold by DEGUSSA, Francfort, FRG.)

Such technique is described in the following references:

W. J. M. DUIMEL et al. in Vox Sang. 23; 249-255; 1972;

J. PILLOT et al in J. Clin. Microbiol. 4; 205-207; 1976 and in Molec. Immunol. 21; 53-60; 1984.

F. BARIN et al. in Ann. Microbiol. (Inst. Pasteur) 129B; 87-100; 1978 which teach that at best only a fraction (i.e. about 60%) of the adsorbed HBsAg is recovered (the best results being obtained by elution with a low ionic strength buffer) unless some amount of deoxycholate be added to the eluant.

In another study (SIEBKE et al. in Acta Path. Microbiol. Scand. Section B; 80; 935-936; 1972), it has been pointed out that Australian antigen is partly eluted from Aerosil by 2% Tween 80 and, likewise, is poorly adsorbed in the presence of the detergent.

DESCRIPTION OF THE INVENTION

When the previously known technique involving adsorption to silica gel and desorption with deoxycholate buffer is applied to a supernatant resulting from the lysate of post-culture HBsAg producing cells obtained by addition of a non ionic detergent, it has been noticed that, not only it is not possible to obtain a clear supernatant of the disrupted cells but the use of deoxycholate buffer for the desorption from colloidal silica does only lead to partial desorption of HBsAg; on the contrary, there is a breakdown of the yeast particle as shown by chromatography on Sepharose 4B-Cl since no hepatitis antigen is then detected at the usual position (Kd: 0.25).

By gradient centrifugation in sucrose it has also been found that, when the disruption of the yeast cells is performed in the presence of 0.5% (w/v) Triton X-100, the structure of the HBsAg particle does not remain intact whereas when 0.5% (v/v) of a polysorbate (e.g. polysorbate 20) is substituted for Triton X-100, the yield of intact HBsAg is substantially improved.

Moreover, it has now also been found that, when the supernatant of yeast cells disrupted with a polysorbate non ionic detergent (e.g. polysorbate 20 or 80) is supplemented with urea—made up to a final concentration from 2 to 6M,—there is obtained (e.g. by stirring for 30 minutes at room temperature) a partially clarified solution.

Furthermore, it has also been found that, upon treatment of the clarified solution with Aerosil, the HBsAg can be completely desorbed therefrom with a low ionic strength buffer system when an urea/non ionic detergent additive is substituted for the previously used desoxycholate additive.

The completeness of HBsAg desorption performed by this way has been shown by the absence of a 22K band in desorbed colloidal silica and it has been confirmed that the isolated HBsAg is assembled into particles of about 22 nm which induce high level of HBsAg antibodies upon parenteral administration to laboratory animals.

Thus, it is a first object of the present invention to provide an improved method for preparing hepatitis B surface antigen valuable for vaccinal purpose from a culture of engineered yeast cells having expressed HBsAg which process comprises disrupting the cells in the presence of a non ionic detergent—more particularly a polysorbate (e.g. 0.3% v/v polysorbate 20 or 80)—and adding thereto urea up to final concentration 2-6M, to yield a clarified HBsAg solution (e.g. by stirring for 30 minutes at room temperature) adsorbing the HBsAg on colloidal silica (such as AEROSIL) (e.g. by stirring overnight at 4° C.), desorbing HBsAg at 37° C. at a pH comprised between 8 and 9.5 with a low ionic strength buffer (e.g. 10 mM) supplemented with urea at final concentration 8M and with a non ionic detergent, more particularly a polysorbate (e.g. polysorbate 20 or 80 at a final concentration 0.1-1% v/v).

The desorbate contains purified HBsAg particles which can be further processed according to any technique well known to the art, e.g. ultrafiltration, chromatography on agarose, precipitation with dextran sulfate/calcium chloride and dialysis.

The invention is illustrated by the following examples.

EXAMPLE 1

Pelleted cells (80 g wet cells weight) of an engineered yeast strain culture expressing HBsAg which have grown up to 30 g dry cells weight per liter of culture are suspended in 150 ml of $Na_2HPO_4$ aqueous solution (7.098 g/l). This suspension is supplemented with 3 ml 4% (w/v) EDTA solution, 0.9 ml polysorbate 20 and 90 ml isopropanol containing 60 mg phenylmethylsulfonyl fluoride (PMSF). The pH is adjusted to 8.1 with NaOH (10% w/v in water). The suspension is refrigerated in an ice bath and disrupted by 2 passages through a cooled glassbead homogenizer. The homogenate is then centrifuged for 30 minutes at 13,000 g.

The crude extract supernatant (160 ml) is made up to a final concentration of 4M urea and stirred for 30 minutes at room temperature to detach HBsAg particles from contaminating yeast cell membranes and AEROSIL ®380 (2.5% w/v) prewashed in 50 mM phosphate buffer ($NaH_2PO_4$/NaOH) pH 7.2 containing 0.3% (v/v) polysorbate 20 and 4M urea is added thereto. The solution is stirred overnight at 4° C. to allow maximal adsorption of HBsAg particles on the silica particles.

The colloidal silica is then centrifuged for 15 minutes at 6500 g and washed twice with 250 ml portions of 10% (w/v) NaCl.

The washed silica is suspended in 80 ml of 10 mM borate buffer pH 9.0 ($Na_2B_4O_7$/HCl) supplemented with 0.5% (v/v) polysorbate 20 and urea (at final concentration 8M) and the suspension is stirred for 4 hours at 37°.

The desorbed colloidal silica is then centrifuged for 30 minutes at 27,000 g to spin down a maximal amount of colloidal silica particles.

Gradient centrifugation in a sucrose gradient as well as electron microscopy show that the antigen is present in particle form having a diameter of about 22 nm.

The desorbate is concentrated to 15 ml in an AMICON DC (an apparatus sold by AMICON CORP. DANVERS, MA, USA) equipped with a cartridge having a cut off of 100,000 daltons and applied to a column (⌀2.5 cm× 100 cm) on SEPHAROSE 4B-Cl (an agarose gel manufactured and sold by PHARMACIA FINE CHEMICALS, Uppsala, Sweden) equilibrated in 10 mM trometamol/HCl buffer (pH 8.0) containing 0.3% (v/v) of polysorbate 20.

The antigen containing peak (Kd=0.25) is treated with dextran sulfate (MW 50,000) at a final concentration 0.1% (w/v) and with $CaCl_2$ at a final concentration of 40 mM.

Excess dextran sulfate is precipitated by dialysis against 40 mM $BaCl_2$ solution in 10 mM trometamol/HCl buffer (pH 8.0). The dialysate (30 ml) is submitted to CsCl gradient centrifugation and the HBsAg containing peak (9 ml) is collected.

The HBsAg purification at the different stages of the hereabove process are summarized in Table II.

Scanning analysis by SDS-PAGE gel shows that the final product is at least 90% pure in HBsAg.

TABLE I

| Fraction | HBsAg (x) (μg) | Proteins (mg) | Poly-saccharides (mg) | Nucleic acids (μg) |
|---|---|---|---|---|
| Crude extract supernatant | 1790 | 954 | 353 | 5300 |
| Concentrated desorbate | 1000 | 49 | 23.5 | 700 |
| Kd 0.25 peak | 328 | 20 | 15 | 780 |
| Dextran sulfate supernatant | 432 | 2.8 | 32 | 724 |
| $BaCl_2$ | 432 | 2.2 | 17.5 | 790 |
| CsCl gradient | 270 | 0.306 | 0.378 | 108 |

(x) by RIA (Radio Immuno Assay)

EXAMPLE 2

Pelleted cells (80 g wet cells weight) of an engineered yeast strain culture expressing HBsAg which have grown up to 30 g dry cells weight per liter of culture are suspended in 150 ml of $Na_2HPO_4$ aqueous solution (7.098 g/l). This suspension is supplemented with 3 ml 4% (w/v) EDTA solution, 0.9 ml polysorbate 20 and 9 ml isopropanel containing 60 mg phenylmethylsulfonyl fluoride (PMSF). The pH is adjusted to 8.1 with NaOH (10% w/v in water). The suspension is refrigerated in an ice bath and disrupted by 2 passages through a cooled glassbead homogenizer. The homogenate is then centrifuged for 30 minutes at 13,000 g.

The crude extract supernatant (160 ml) is made up to a final concentration of 4M urea and stirred for 30 minutes at room temperature to detach HBsAg particles from contaminating yeast cell membranes and AEROSIL® 380 (2.5% w/v) prewashed in 50 mM phosphate buffer ($NaH_2PO_4$/NaOH) pH 7.2 containing 0.3% (v/v) polysorbate 20 and 4M urea is added thereto. The solution is stirred overnight at 4° C. to allow maximal adsorption of HBsAg particles on the silica particles.

The colloidal silica is then centrifuged for 15 minutes at 6500 g and washed twice with 250 ml portions of 10% (w/v) NaCl.

The washed silica is suspended in 80 ml of 10 mM borate buffer pH 9.0 ($Na_2B_4O_7$/HCl) supplemented with 0.5% (v/v) polysorbate 20 and urea (at final concentration 8M) and the suspension is stirred for 4 hours at 37°.

The desorbed colloidal silica is then centrifuged for 30 minutes at 27,000 g to spin down a maximal amount of colloidal silica particles.

The desorbate is dialyzed against 10 mM trometamol/HCl buffer (pH 7.5) in an AMICON DC equipped with a cartridge having a cut-off of 100,000 daltons in order to dialyze out urea and applied to a column of 25 ml of hexylagarose (a product manufactured and sold by PHARMACIA FINE CHEMICALS, Uppsala, Sweden) equilibrated in 10 mM trometamol/HCl buffer (pH 7.5) at a flow rate of 10 ml per hour.

The column is then washed with 10 mM trometamol/HCl buffer (pH 7.5) and eluted with a 50/50 (v/v) mixture of ethylene glycol and 10 mM trometamol/HCl buffer (pH 7.5) supplemented with NaCl at a final concentration 1M and thereafter with 10 mM trometamol/HCl buffer (pH 7.5) supplemented with urea at a final concentration 4M.

The HBsAg purification at the different stages of the hereabove process are summarized in Table II.

TABLE II

| Fraction | HBsAg (1) (mg) | Proteins (mg) | Poly-saccharides (mg) | Nucleic acids (μg) |
|---|---|---|---|---|
| Crude extract | 3.5 | 2224 | 517 | 17.9 |
| Desorbate | 2.1 | 86.4 | 30.1 | 2.1 |
| Ethylene glycol/NaCl eluate | 1.4 | 1.10 | 0.05 | ND (2) |
| Urea eluate | 0.7 | 0.72 | 0 | ND (2) |

(1) by RIA (Radio Immuno Assay)
(2) ND = non detectable

Scanning analysis by SDS-PAGE gel shows that the final product is at least 97% pure in HBsAg.

EXAMPLE 3

The technique is that of Example 2 but 25 ml of phenylagarose (a product manufactured by PHARMACIA FINE CHEMICALS, Uppsala, Sweden) is substituted for the hexyl agarose therein specified.

The HBsAg purification scheme and the HBsAg content of the final product are similar to those given in Example 2.

EXAMPLE 4

The solution of HBsAg obtained at the end of Example 1 was adjusted to a protein content of 10 μg per ml by addition of NaCl, phosphate buffer ($Na_2HPO_4$/$NaH_2PO_4$) and ALHYDROGEL® (an aluminium hydroxide gel manufactured and sold by SUPERPHOS Export Co., Copenhagen, Denmark) up to final concentration of 0.9% (w/v), 20 mM and 0.15% (w/v) of $Al(OH)_3$ respectively, the final pH being 6.9.

The preparation was sterilized and distributed into 2 ml glass vials, each containing a one ml dosage unit of vaccine.

EXAMPLE 5

Different dilutions of dosage units of the vaccine preparation of Example 4 were administered by intraperitoneal route to 5 groups of five-week old Swiss mice.

Twenty eight days after administration, the animals were bled and the serum anti-HBs titres were determined for each sample by the AUSAB® method (AUSAB is the registered trade mark of a test kit manufactured and sold by ABBOTT Diagnostic Products GmbH, Wiesbaden, FRG).

At the same time and following the same vaccination schedule, same dilutions of dosage units of a vaccine preparation obtained by the technique of Example 4 but with an antigen prepared by the technique of Example 1 without the colloidal silica step were also administered to 5 groups of five week old Swiss mice.

The results of this comparative trail are summarized in Table III wherein (A) refers to the vaccine obtained by the technique of the invention urea while (B) refers to the vaccine obtained by the process without colloidal silica step.

TABLE III

| Vaccine preparation | Proteins (mg) | Number of mice | Seroconversion rate (%) | $ED_{50}$ (ng RIA) |
|---|---|---|---|---|
| A | .039 | 10 | 0 | |
|  | .156 | 10 | 60 | |
|  | .625 | 10 | 90 | 180 |
|  | 2.5 | 10 | 90 | |
|  | 10 | 6 | 83 | |
| B | .039 | 10 | 10 | |

TABLE III-continued

| Vaccine preparation | Proteins (mg) | Number of mice | Seroconversion rate (%) | $ED_{50}$ (ng RIA) |
|---|---|---|---|---|
| | .156 | 10 | 10 | |
| | .625 | 10 | 20 | 1954 |
| | 2.4 | 10 | 50 | |
| | 10 | 10 | 80 | |

$ED_{50}$: effective dose in 50% of the treated animals
RIA: Radio Immuno Assay

What we claim is:

1. A method for the isolation and purification of hepatitis B surface antigen by treatment with colloidal silica of the supernatant of engineered yeast cells having produced said antigen and disrupted in the presence of a non ionic detergent which is more particularly a polysorbate which comprises clarifying the supernatant by addition of urea, adsorbing the antigen on the colloidal silica, desorbing therefrom the antigen with a low ionic buffer (pH 8-9.5) supplemented with urea and with a non ionic detergent.

2. A method according to claim 1 wherein the clarification of the supernatant is performed by addition of urea up to a final concentration comprised between 2 and 6M.

3. A method according to claim 1 or 2 wherein the clarification step is performed at 4° C.

4. A method according to claim 1 or 2 wherein the low ionic strength buffer is 10 mM.

5. A method according to claim 2 wherein urea is supplemented to the low ionic buffer up to a final concentration 8M.

6. A method according to claim 2 or 5 wherein the desorption is performed at 37° C.

7. A method according to claim 2 wherein the non ionic detergent supplemented to the low ionic strength buffer is a polysorbate.

8. A method according to claim 7 wherein the polysorbate is polysorbate 20 or 80.

9. A method according to claim 7 wherein the final concentration in polysorbate is comprised between 0.1 and 1% (v/v).

* * * * *